United States Patent [19]
Uchida et al.

[11] Patent Number: 6,057,141
[45] Date of Patent: May 2, 2000

[54] DNA ENCODING THE SUBUNIT OF AVIAN LACTATE DEHYDROGENASE

[75] Inventors: Kohji Uchida, Shiga-ken; Hirokazu Matsukawa, Osaka; Tuyosi Fujita, Osaka; Yushi Matuo, Osaka, all of Japan

[73] Assignee: Oriental Yeast Co., Ltd., Japan

[21] Appl. No.: 09/128,967

[22] Filed: Aug. 4, 1998

Related U.S. Application Data

[62] Division of application No. 08/869,506, Jun. 5, 1997, Pat. No. 5,827,710.

[51] Int. Cl.⁷ .............................. C12N 9/04; C12N 5/00; A23J 1/00
[52] U.S. Cl. .................... 435/190; 435/349; 435/254.21; 530/412
[58] Field of Search .............................. 435/190, 254.21, 435/349; 530/412

[56] References Cited

FOREIGN PATENT DOCUMENTS 8-289  8/1996  Japan .

OTHER PUBLICATIONS

Clinical Chemistry, Supplement No. 2 to vol. 23, 1994, 141b "Heat Resistant Lactose Dehydrogenase".
Torff et al, 1977, In Sund, H. (ed). "Pyridine Nucleotide Dependent Dehydrogenase" pp. 31–42.
Voorter, C.E.M. et al (1993) Eur. J. Biochem. 211:643–648.
Hendriks et al (1988) Duck lens ε–crystallin and lactate dehydrogenase B4 are identical: A single–copy gene product with two distinct functions Proc. Natl. Acad. Sci. USA 85: 7114–7118.
Hirota et al (1990) Nucleotide and deduced amino acid sequences of chicken lactate dehydroenase–A. Nucl. Acids Res. 18 (21): 6432.

*Primary Examiner*—Lisa J. Hobbs
*Attorney, Agent, or Firm*—Nixon & Vanderhye

[57] ABSTRACT

The present invention provides a gene encoding the type B subunit protein of avian lactate dehydrogenase. The gene encoding the type B subunit protein of avian lactate dehydrogenase of the present invention is obtained by plaque hybridization or the like from a cDNA library derived from avian heart muscle and encodes the type B subunit protein of avian lactate dehydrogenase having an amino acid sequence shown as SEQ ID NO. 2.

1 Claim, 11 Drawing Sheets

Fig. 2

```
                        R   Q   Q   E   G   E   S
SENSE PRIMER :    5'  CTGGTTCGGCCCA CGT CAG CAA GAA GGA GAA AG- 3'

V   Q   K   H   V   E   K
ANTISENSE PRIMER :  5'  CTCGCTCGCCCCA -AC CTG CTT GTG AAC CTC CTT 3'
```

Fig. 4

SENSE PRIMER :

```
              M   A   T   L   K   E
5' CCGGAATTC ATG GCG ACC CTG AAG GAG 3'
   ‾‾‾‾‾‾‾‾
    EcoRI
```

ANTISENSE PRIMER :

```
              *   *   L   D   K   L   D
5' CCCGGATCC CTA TTA CAG ATC TTT AAG ATC 3'
   ‾‾‾‾‾‾‾‾
    BamHI
```

★ : TERMINATION CODON

```
  -54         CCACGGTCACGGTACTGCTCCCGGTTCTCCTTTCACCGCACCGATCCGGACGTT

1  ATGGCGACCCTGAAGGAGAAGCTGATCGCCCCGTGGCCGCGGGCAGCACGGTTCCCAGC
    1  MetAlaThrLeuLysGluLysLeuIleAlaProValAlaAlaGlySerThrValProSer

61  AACAAGATCACCGTGGTGGGGGTCGGGCAGGTGGGGATGGCGTGTGCCATCAGCATCCTC
   21  AsnLysIleThrValValGlyValGlyGlnValGlyMetAlaCysAlaIleSerIleLeu

121  GGCAAGGGTCTTTGTGATGAGCTTGCTCTGGTTGATGTTTTGGAAGACAAGCTAAAAGGA
   41  GlyLysGlyLeuCysAspGluLeuAlaLeuValAspValLeuGluAspLysLeuLysGly

181  GAAATGATGGATCTACAGCATGGCAGCTTGTTCCTTCAGACTCATAAGATTGTGGCAGAC
   61  GluMetMetAspLeuGlnHisGlySerLeuPheLeuGlnThrHisLysIleValAlaAsp

241  AAAGATTATGCTGTCACAGCCAACTCCAAGATTGTGGTAGTAACTGCAGGTGTTCGTCAG
   81  LysAspTyrAlaValThrAlaAsnSerLysIleValValValThrAlaGlyValArgGln

301  CAAGAGGGGGAGAGTCGTCTCAACCTGGTTCAGAGGAATGTGAACGTCTTCAAATTCATC
  101  GlnGluGlyGluSerArgLeuAsnLeuValGlnArgAsnValAsnValPheLysPheIle

361  ATTCCTCAGATTGTGAAATACAGCCCCAATTGCACTATCCTTGTGGTTTCCAACCCAGTG
  121  IleProGlnIleValLysTyrSerProAsnCysThrIleLeuValValSerAsnProVal

421  GATATATTAACCTATGTCACATGGAAGCTGAGTGGCCTGCCAAAGCACCGTGTGATTGGA
  141  AspIleLeuThrTyrValThrTrpLysLeuSerGlyLeuProLysHisArgValIleGly

481  AGTGGCTGCAATCTAGACACAGCTAGATTCCGCTACCTGATGGCTGAGAGACTTGGTATC
  161  SerGlyCysAsnLeuAspThrAlaArgPheArgTyrLeuMetAlaGluArgLeuGlyIle

541  CACCCAACCAGCTGCCATGGCTGGATTTTAGGAGAACATGGTGATTCTAGTGTGGCTGTT
  181  HisProThrSerCysHisGlyTrpIleLeuGlyGluHisGlyAspSerSerValAlaVal

601  TGGAGCGGAGTTAATGTGGTAGGTGTTTCTCTCCAGGAGCTGAATCCTGCCATGGGAACT
  201  TrpSerGlyValAsnValValGlyValSerLeuGlnGluLeuAsnProAlaMetGlyThr

661  GACAAAGACAGCGAGAACTGGAAGGAAGTCCACAAGCAGGTTGTTGAAAGTGCCTATGAG
  221  AspLysAspSerGluAsnTrpLysGluValHisLysGlnValValGluSerAlaTyrGlu

721  GTAATCAGACTCAAGGGGTATACGAACTGGGCCATTGGTCTTAGCGTTGCCGAGCTCTGT
  241  ValIleArgLeuLysGlyTyrThrAsnTrpAlaIleGlyLeuSerValAlaGluLeuCys

781  GAGACAATGCTGAAGAACTTGTACCGAGTTCATTCTGTGTCAACACTGGTAAAGGGCACA
  261  GluThrMetLeuLysAsnLeuTyrArgValHisSerValSerThrLeuValLysGlyThr

841  TATGGCATTGAGAACGATGTCTTCCTGAGCCTGCCTTGTGTCCTGAGTGCCTCTGGATTG
  281  TyrGlyIleGluAsnAspValPheLeuSerLeuProCysValLeuSerAlaSerGlyLeu

901  ACAAGTGTCATCAACCAAAAGCTGAAGGATGATGAAGTGGCTCAGCTGAAGAAGAGTGCA
  301  ThrSerValIleAsnGlnLysLeuLysAspAspGluValAlaGlnLeuLysLysSerAla

961  GACACATTGTGGAGCATCCAGAAAGATCTTAAAGATCTGTAATTCAAATGTTAGATTGCA
  321  AspThrLeuTrpSerIleGlnLysAspLeuLysAspLeu***

1021  GCAATAGGAAAACAGCGTGTTGTGCACAAATGTGGGCTCTCTACTCACTATACATCTCTG

1081  TGGTTAACATTTAATGCTCTTCCAGACTGAGCTTTTGTCCACGGTAGCTAAACATAAGCT

1141  TGCTGTAACGCACAGACCTTATGAACAAATAAAGCAACTTTCAGGC
```

```
1         10        20        30        40        50        60
ATLKEKLITPVAAGSTVPSNKITVVGVGQVGMACAISILGKGLCDELALVDVLEDKLKGE
--------A---------------------------------------------------

70        80        90        100       110       120
MMDLQHGSLFLQTHKIVADKDYAVTANSKIVVVTAGVRQQEGESRLNLVQRNVNVFKFII
------------------------------------------------------------

130       140       150       160       170       180
PQIVKYSPNCVILVVSNPVDILTYVTWKISGLPKERVIGSGCNLDTARFRYLMAERIGIE
-----------T------------------------------------------------

190       200       210       220       230       240
PTSCHGWILGEHGDSSVAVWSGVNVAGVSLQQLDFAMGTDKDSENWKEVHKQVVESAYEV
------------------------------V-----E-N---------------------

250       260       270       280       290       300
IRLKGYTNWAIGLSVAELCETMLKNLYRVHSVSTLVKGTYGIENDVFLSLPCVLSASGLT
------------------------------------------------------------

310       320       330
SVINQKLKDDEVAQLKKSADTLWSIQKDLKDL
-------------------------------
```

UPPER LINE: AMINO ACID SEQUENCE DIRECTLY
DETERMINED FROM THE PROTEIN
(TORFF, H.J. ET AL.(1977) IN SUND, H.(ED),
PYRIDINE NUCLEOTIDE DEPENDENT DEHYDROGENASE,
WAITHER DE GRUYTER, BERLIN, PP. 31-42.)

LOWER LINE: AMINO ACID SEQUENCE PRESUMED
FROM THE NUCLEOTIDE SEQUENCE

DNA ENCODING THE SUBUNIT OF AVIAN LACTATE DEHYDROGENASE

This is a division of application Ser. No. 08/869,506, filed Jun. 5, 1997, now U.S. Pat. No. 5,827,710.

BACKGROUND OF THE INVENTION

The present invention relates to genes encoding the type B subunit protein of avian lactate dehydrogenase.

Lactate dehydrogenase (LDH) is an enzyme which dehydrogenates lactic acid into pyruvic acid in conjunction with the hydrogen acceptor $NAD^+$ and which exists widely in a variety of animal tissues and microorganisms as an enzyme serving to produce lactic acid from pyruvic acid in the glycolytic pathway.

Particularly, it is known that animal LDH is grouped into two subunits, type A (type M or skeltal muscle type) and type B (type H or heart muscle type), which results in a variation of enzymological properties between LDH isozymes. The subunits homogeneously or heterogeneously form tetrameric isozymes called as $LDH_1(B_4)$, $LDH_2(A_1B_3)$, $LDH_3(A_2B_2)$, $LDH_4(A_3B_1)$, $LDH_5(A_4)$ in descending order of electric mobility toward the anode side. Distributions of each isozyme in a body are uneven, e.g. $LDH-B_4$ is found at higher level in heart muscle, red blood cells and kidney while $LDH-A_4$ is found at higher level in skeltal muscle and liver. $LDH-A_2B_2$ is found at higher level in prostate gland, colon, thyroid and lung tissues. In recent years, the presence of types C and D subunits has newly been identified, and $LDH-X(C_4)$ has been detected in testis and sperms as well as $LDH-Z(D_4)$ in choriocarcinoma and metastasis lesions thereof.

LDH has been used especially in the field of clinical test reagents 1) as a coupling enzyme for determining the enzymatic activity of various amino-transferases such as alanine aminotransferase (ALT) in UV spectrometry of the produced pyruvic acid, 2) as a coupling enzyme converting various substrates such as urea into pyruvic acid in UV spectrometry of the produced pyruvic acid, and 3) for eliminating endogenous pyruvic acid in a subject. Particularly, the determination of aminotransferase activity using LDH as mentioned in 1) is widely adopted as a clinical test, because amino-transferases are enzymes which show high activity in liver, heart, kidney, etc. and remarkably increase in serum during various diseases.

It is preferable for clinical test reagents to be stable in a liquid state rather than a powder state in view of convenience. Porcine $LDH-B_4$ has been commonly used as a clinical test reagent for determining amino-transferase activity because it is abundantly available, but it was disadvantageously difficult to store stably in a liquid state for a long period.

Recently, $LDH-B_4$ derived from birds has been found to show remarkable heat stability in solution even in a pH range ensuring the stability of the coenzyme (NADH), such as a pH of about 9 to 10. The $LDH-B_4$ derived from birds has the almost same enzymatic properties as the prior porcine $LDH-B_4$ and does not cause any special problem in the determination sensitivity when it is used as a reagent for determining transaminase activity. Therefore, the $LDH-B_4$ derived from birds is expected to be sufficiently useful as an enzyme for clinical tests from its stability in solution and enzymatic properties (Japanese Patent Public Disclosure: No. 289/1996 "Transaminase Determination Reagent"; and "Heat Resistant Lactate Dehydrogenase Appropriate to Liquid ALT Determination Reagent", Clinical Chemistry, Supplement, No. 2 to Vol. 23,, 1994, 141b).

However, it is difficult to practically use the natural $LDH-B_4$ protein prepared from birds as a clinical test enzyme because it can be obtained only in a small amount. Thus, it is important to clone a LDH-B gene derived from birds so that a large amount of $LDH-B_4$ protein may be expressed by genetic engineering techniques.

SUMMARY OF THE INVENTION

The present invention provides an isolated gene encoding the type B subunit (cLDH-B) protein of LDH derived from birds, for example, chicken.

The present invention also provides an expression vector for expressing the cLDH-B protein containing said gene.

The present invention also provides a host cell transformed with said expression vector.

The present invention further provides a recombinant cLDH protein expressed by said host cell. Namely, the cLDH-B subunit is expressed by said expression vector and forms a tetramer in said host cell to provide the $cLDH-B_4$ isozyme.

After in depth studies, the inventors isolated cDNA encoding the type B subunit protein of chicken LDH and determined its base sequence. As a result, a putative amino acid sequence (SEQ ID NO. 2) encoded by the isolated cDNA was identical with the amino acid sequence of the known natural cLDH-B protein shown as SEQ ID NO. 3 except for five amino acid residues (Troff, H. J. et al. (1977), In Sund, H. (ed.), Pyridine Nucleotide Dependent Dehydrogenase. Walther de Gruyter, Berlin, pp.31–42). As used herein, the term "cLDH-B" means the type B subunit of chicken LDH, but may sometimes refer to the type B subunit of avian LDH according to the context.

BRIEF DESCRIPTION OF THE DRAWINGS

FIG. 2 shows PCR primers for amplifying the type A subunit cDNA fragment of chicken LDH.

FIG. 4 shows PCR primers for subcloning the type B subunit cDNA of chicken LDH.

FIG. 5 shows the nucleic acid sequence of the type B subunit cDNA of chicken LDH and a putative amino acid sequence of the type B subunit protein of chicken LDH encoded by said cDNA.

FIG. 6 shows the amino acid sequence of the type B subunit of chicken LDH.

DETAILED DESCRIPTION OF THE INVENTION

Avian LDH-type B Subunit Gene

Figure 1:
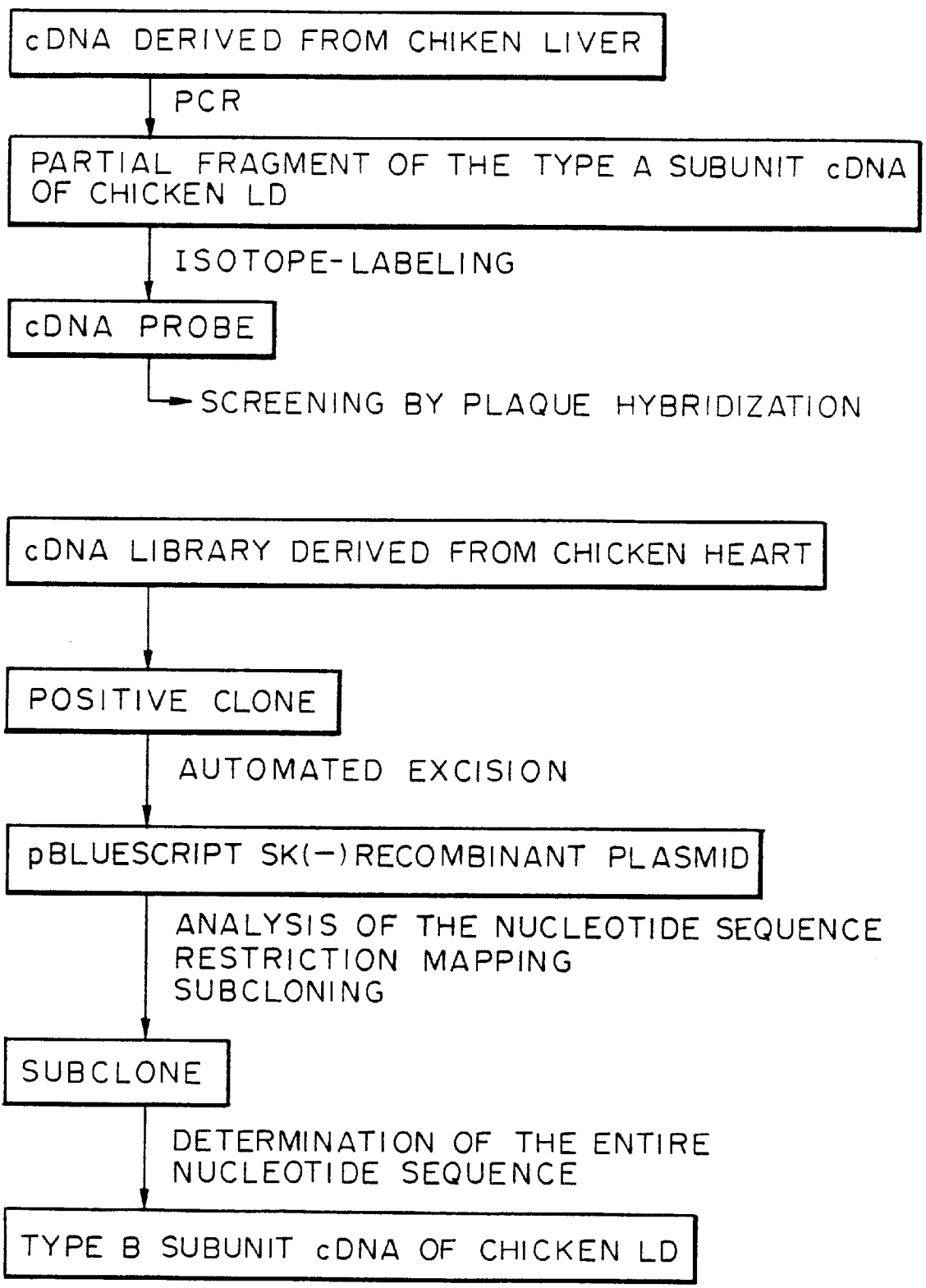
FIG. 1 shows a summary of the cloning strategy of the type B subunit cDNA of chicken LDH used in the present invention.

The cLDH-B gene of the present invention is DNA encoding a protein having the amino acid sequence shown as SEQ ID NO. 2 of the Sequence Listing or a protein wherein one or more amino acids are added, deleted or substituted from said amino acid sequence, and having the biological activity of the cLDH-B. The amino acid sequence shown as SEQ ID NO. 2 differs by five amino acid residues from the amino acid sequence of the natural chicken LDH type B subunit protein shown as SEQ ID NO. 3. This difference is considered to be attributed to 1) difference of analysis methods, 2) base substitutions during the cloning process of cDNA, 3) heterogeneity of gene, or other factors.

The amino acid sequence of the cLDH-B protein shown as SEQ ID NO. 3 has the 73.3% homology with the amino acid sequence of the type A subunit protein of chicken LDH. Homologies between the amino acid sequence of the chicken LDH-B protein and those of the corresponding human, porcine and murine type B subunit proteins are 89.5%, 88.9% and 88.3%, respectively.

The base sequence of the gene encoding the cLDH-B protein determined by the present invention is shown in SEQ ID NO. 1 along with a putative amino acid sequence encoded thereby. As is apparent from this sequence, this cDNA consists of a total of 1002 base pairs counted from the base numbers 1 to 1002. The base numbers 1 to 3 represent a translation initiation genetic codon, while the base numbers 1000 to 1002 represent a translation termination genetic codon. The sequence of the base numbers 1000 to 1002 (***) may be any of TAA, TGA or TAG. The SEQ ID NO. 2 represents an amino acid presumed from the base sequence shown as SEQ ID NO. 1.

The gene of the present invention is available from the yeast host cells Saccharomyces cerevisiae internationally deposited under Accession No. FERM BP-5292 on Nov. 13, 1995, to the National Institute of Bioscience and Human Technology of the Agency of Industrial Science and Technology of the Ministry of International Trade and Industry in Japan (YRp1G-cLD-B). If desired, the gene of the present invention may be obtained from a cDNA library derived from chicken heart mRNA by using, for example, plaque hybridization technique as described below in Examples, or may be readily prepared by PCR technique using a cDNA library derived from chicken heart mRNA as a template or RT-PCR technique using chicken heart mRNA as a starting material on the basis of the DNA sequence determined by the present invention. In these techniques, the chicken heart mRNA may be replaced by heart mRNA derived from other birds including poultry such as quail, goose, duck, gull, pigeon, etc. In those cases, the cDNA corresponding to the cLDH-B derived from the selected bird is obtained. Thus prepared cLDH-B cDNA can also be used to prepare a variant by the method described below.

Because a plurality of codons exist which encode one amino acid, DNAs of any nucleotide sequence which encodes the same amino acid sequence are included in the scope of the present invention. Therefore, any DNA encoding the amino acid sequence shown as SEQ ID NO. 2 is included in the scope of the present invention.

Further, it is well known that in general a peptide which has a physiological activity may sometimes maintain its physiological activity even if the amino acid sequence of said peptide is somewhat modified, i.e. even if one or more amino acids in said amino acid sequence are substituted or deleted or one or more amino acids are added. Therefore, DNA encoding a variant of the cLDH-B of the amino acid sequence shown as SEQ ID NO. 2 bearing such a modification but having the biological activity of the cLDH-B is also included in the scope of the present invention. For example, DNA encoding the amino acid sequence shown as SEQ ID NO. 3 is evidently included in the scope of the present invention. The expression "having the biological activity of the cLDH-B" means having an activity to form a tetramer between subunits of the type B or subunits of other types such as the type A, thereby dehydrogenating lactic acid into pyruvic acid in conjunction with the hydrogen acceptor $NAD^+$.

The variant bearing an addition, deletion or substitution of amino acids can be prepared by applying, for example, well known site-directed mutagenesis technique to, for example, DNA encoding it (for example, Nucleic Acid Research, Vol. 10, No. 20, pp. 6487–6500, 1982). As used herein, the expression "one or more amino acids" means such a number of amino acids as can be added, deleted or substituted by site-directed mutagenesis technique.

Site-directed mutagnesis technique can be applied in the following manner by using, for example, a synthetic oligonucleotide primer which is complementary to the single-stranded phage DNA to be mutated except for a specific disparity corresponding to the desired variation. Namely, such a synthetic oligonucleotide is used as a primer to synthesize a strand complementary to the phage, and the resulting double-stranded DNA is transformed into a host cell. The culture of the transformed cell is plated on agar so that a single cell containing the phage forms a plaque. Theoretically 50% of new colonies contain modified single-stranded phages while the remaining 50% have the original sequence. Thus formed plaques are hybridized with a synthetic probe labeled with a radioisotope or the like at a temperature which allows hybridization with DNA completely identical with those having said desired variation but not with dissimilar DNA having the original strand. Then, the plaques which hybridize to said probe are collected and cultured to recover DNA.

Alternatives to the above site-directed mutagenesis for introducing a substitution, deletion or insertion of one or more amino acids into the amino acid sequence of a biologically active peptide such as enzyme without affecting its activity are a method for treating the gene with a mutagen and a method for selectively cleaving the gene, then removing, adding or substituting a selected nucleotide, and then ligating it. Both ends of the DNA of the present invention described above, i.e. the translation initiation codon and the translation termination codon can each be ligated to any DNA fragment. The size of the nucleotide sequence of this DNA fragment is not critical, so far as a suitable DNA fragment to be ligated to an extranuclear gene carried on bacteria or the like may be provided.

The variant may contain a conservatively substituted sequence, which means that a specific amino acid residue may be replaced with a residue having similar physico-chemical characteristics. Non-limitative examples of conservative substitution include a substitution between aliphatic group-containing amino acid residues such as a mutual substitution between Ile, Val, Leu or Ala or a substitution between polar group-containing amino acid residues such as Lys and Arg.

The nucleotide sequence within the scope of the present invention includes isolated DNA and RNA which hybridize to the cLDH-B base sequence disclosed herein under the conditions of mild or strict stringency and encode the biologically active cLDH-B protein. The hybridization conditions of mild stringency mean, for example, the conditions described in Sambrook et al., Molecular Cloning: A Laboratory Manual, 2 ed. Vol. 1, pp. 1. 101–104, Cold Spring Harbor Laboratory Press, (1989). As defined by Sambrook et al., the hybridization conditions of mild stringency include the use of a prewashing solution of 5×SSC, 0.5% SDS, 1.0 mM EDTA (pH 8.0) and a hybridization condition at about 55° C. in 5×SSC overnight. The conditions of strict stringency include hybridization and washing at higher temperatures. In this case, the temperature and the salt concentration of the washing solution are appropriately adapted to various factors such as the length of the probe.

Preparation of the Type B Subunit Polypeptide of Recombinant Avian LDH

The present invention also provides an expression vector containing the cLDH-B cDNA and a process for preparing a recombinant cLDH-B polypeptide by culturing a host cell containing said expression vector under the conditions suitable for the expression of the cLDH-B polypeptide and recovering thus expressed cLDH-B.

In order to prepare the recombinant cLDH-B polypeptide of the present invention, a cLDH-B DNA sequence and linked to a suitable transcription or translation control nucleotide sequence derived from a mammalian, microbial, viral or insect gene or the like, is inserted into an expression vector selected according to the host cell used. Examples of the control sequence include transcription promoter, operator or enhancer, mRNA ribosome-binding site, and suitable sequences controlling the initiation and termination of transcription and translation. In addition, a sequence encoding a suitable signal peptide which is not originally present in the cLDH-B gene may be integrated into the expression vector.

Host cells suitable for the expression of the cLDH-B polypeptide include procaryotic, yeast or higher eucaryotic cells. Suitable cloning and expression vectors used in bacterial, fungal, yeast and mammalian cell hosts are described in, for example, Pouwels et al., Cloning Vectors: A Laboratory Manual, Elsevier, N.Y., (1985).

The most preferable host cells are yeast cells. The genus Saccharomyces (for example, S. cerevisiae) is preferably used, but other yeast genera such as Pichia or Kluyveromyces may also be used. Yeast vectors often contain a sequence of replication origin from the 2 µ yeast plasmid, an autonomous replication sequence (ARS), a promoter region, a sequence for polyadenylation, a sequence for the termination of transcription, and a selectable marker gene. The promoter sequence suitable for yeast vectors includes, among others, metallothionein, 3-phosphoglycerate kinase (Hitzeman et al., J. Biol. Chem. 255:2073, 1980) or other enzymes for glycolysis (Hess et al., J. Adv. Enzyme Reg. 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triose-phosphate isomerase, phosphoglucose isomerase and glucokinase. Other vectors and promoters suitably used for the expression in yeasts are described in Hitzeman, EPA-73,657. Another alternative is the glucose-supressed ADH2 promoter described by Russell et al. (J. Biol. Chem. 258:2674, 1982) and Beier et al. (Nature 300:724, 1982). A shuttle vector which is replicable in the both of yeasts and E. coli can be constructed by inserting a DNA sequence from pBR322 for selection and replication in E. coli (Amp$^r$ gene and a replication origin) into one of said yeast vectors.

The cLDH-B polypeptide can be secreted by using the yeast α-factor leader sequence. The α-factor leader sequence is often inserted between a promoter sequence and a structural gene sequence. For example, see Kurjan et al., Cell 30:933, 1982; Bitter et al., Proc. Natl. Acad. Sci. USA 81:5330, 1984; U.S. Pat. No. 4,546,082; and EP No. 324, 274. Other leader sequences suitable for promoting secretion of the recombinant polypeptide from yeast hosts are also known. The leader sequence may be modified near the 3' end to contain one or more restriction sites. This may ease the ligation of the leader sequence to a structural gene.

Transformation procedures of yeasts are known. One of the procedures is described in Hinnen et al., Proc. Natl. Acad. Sci. USA 75:1929, 1978. The procedure of Hinnen et al. involves selecting Trp$^+$ transformants in a selection medium consisting of 0.67% yeast nitrogen base, 0.5% casamino acid, 2% glucose, 10 µg/ml adenine and 20 µg/ml uracil.

In order to induce expression, yeast host cells transformed with a vector containing an ADH2 promoter sequence may be grown in a "rich" medium. An example of the rich medium consists of 1% yeast extract, 2% peptone and 1% glucose supplemented with 80 µg/ml adenine and 80 µg/ml uracil. Derepression of the ADH2 promoter occurs when glucose has been exhausted from the medium.

Figure 7:
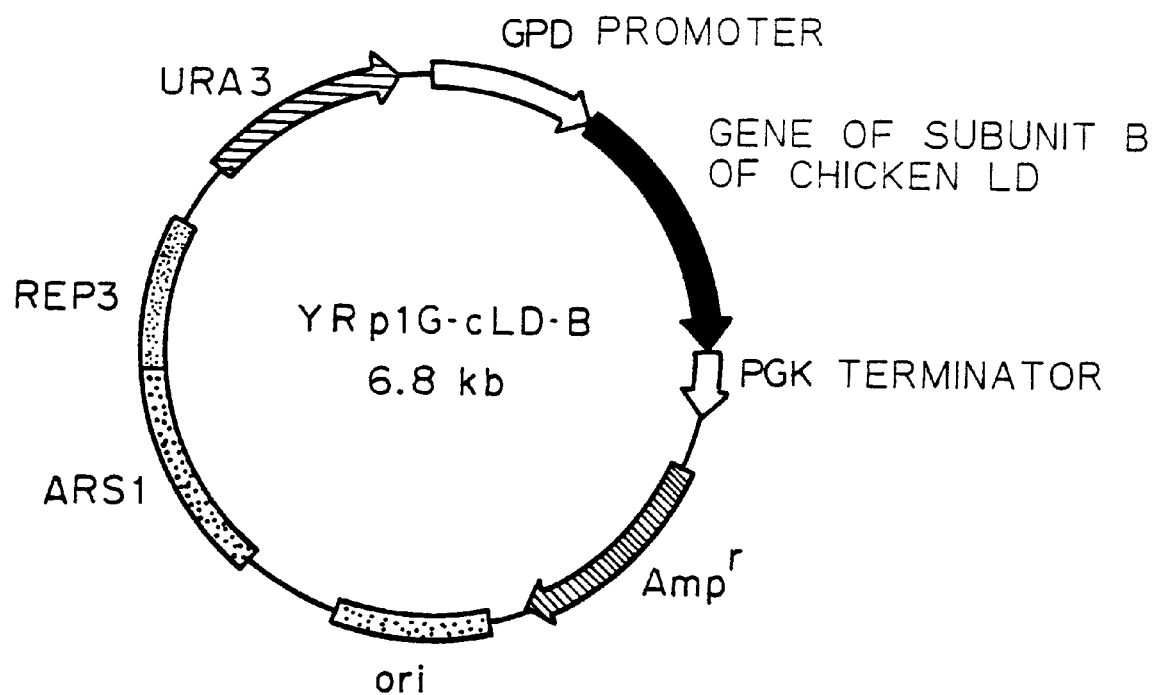
FIG. 7 shows a schematic view of the yeast expression plasmid YRp1G-cLD-B for the chicken $LDH-B_4$.

A preferred yeast expression vector for producing the recombinant cLDH-B$_4$ protein of the present invention is, for example, YRp1G-cLD-B as shown in FIG. 7. Host cells transformed with YRp1G-cLD-B have been internationally deposited according to the Budapest Treaty under Accession No. FERM BP-5292 as described above.

The cLDH-B may also be expressed in a procaryotic organism. The procaryotic organism includes gram-negative and gram-positive bacteria, such as E. coli or Bacillus subtilis. In procaryotic cells such as E. coli, the cLDH-B polypeptide may contain an N-terminal methionine residue to facilitate the expression of the recombinant polypeptide even in procaryotic cells. This N-terminal Met can be removed from the recombinant cLDH-B polypeptide by a known method after expression.

The expression vectors used in procaryotic host cells generally contain one or more phenotype selectable marker genes. The phenotype selectable marker gene is, for example, a gene conferring resistance to antibiotics or autotrophy. Examples of the expression vectors suitable for procaryotic host cells include commercially available plasmids such as pBR322 (ATCC37017) or derivatives thereof. The pBR322 ease the identification of the transformed cells because it contains genes for resistance to ampicillin and tetracycline. A suitable promoter and the cLDH-B DNA sequence are inserted into this pBR322 vector. Other commercially available vectors include, for example, pKK223-3 (Pharmacia Fine Chemicals of Uppsala, Sweden) and pGEM1 (Promega Biotec of Madison, Wis., USA).

Promoter sequences commonly used in expression vectors for procaryotic host cells include β-lactamase (penicillinase), lactose promoter (Chang et al., Nature 275:615, 1978; and Goeddel et al., Nature 281:544, 1979), etc. Especially useful procaryotic host cell expression systems incorporate the phage λP$_L$ promoter and cI857ts non-heat resistant repressor sequences. Plasmid vectors incorporating a derivative of the λP$_L$ promoter which are available from American Type Culture Collection include the plasmids pHUB2 (present in the E. coli strain JMB9 (ATCC37092)) and pPLc28 (present in the E. coli strain RP1 (ATCC53082)).

The recombinant cLDH-B polypeptide may also be expressed using a mammalian or insect host cell culture system. Strained cell systems derived from mammals may also be used. The transcription and translation control sequences for mammalian host cell expression vectors can be obtained from viral genomes. Commonly used promoter sequence and enhancer sequence are derived from polyoma virus, adenovirus 2 or the like. Other genetic elements may be provided for the expression of a structural gene sequence in mammalian host cells using an SV40 viral genome such as a DNA sequence derived from an SV40 origin, early and late promoters, an enhancer, splice sites and a polyadenylation site. The expression vectors for use in mammalian host cells can be constructed by, for example, the method of Okayama and Berg (Mol. Cell. Biol. 3 :280, 1983).

The recombinant cLDH-B protein can be produced by culturing host cells transformed with an expression vector containing DNA encoding the cLDH-B protein under the conditions allowing the expression of the cLDH-B protein. The produced recombinant cLDH-B subunits form the tetrameric cLDH-$B_4$ isozyme. Then, the recombinant cLDH-B protein is recovered from the culture medium or cell extract depending on the expression system used. The operation for purifying the cLDH-B protein may be determined as appropriate depending on the factors such as the type of the host cell used and whether or not the cLDH-B protein is secreted into the culture medium.

The recombinant cLDH-B protein produced in a bacterial host normally exists in the host cells and, therefore, at first the cells are disrupted to separate cell precipitate or supernatant by centrifugation or filtration or the like, and then the protein is isolated by appropriate combinations of concentration, salting out, ion exchange, affinity purification or gel filtration purification. Finally, RP-HPLC may be used for the final purification step. The disruption of the microbial cell host can be accomplished by an appropriate conventional method including the repetition of freezing and thawing, sonication, mechanical disruption or the use of a cytolytic agent.

When a transformed yeast host is used, the cLDH-$B_4$ can be expressed preferably as secreted polypeptide. This simplifies purification. The recombinant polypeptide secreted in the fermentation supernatant of yeast host cells can be purified by analogues to the method disclosed by Urdal et al. (J. Chromatog 296:171, 1984). Urdal et al. describes two successive reverse phase HPLC steps using a preparative HPLC column for the purification of the recombinant cLDH-$B_4$.

Thus obtained recombinant cLDH-$B_4$ protein can be used in the field of clinical test reagents, for example, 1) as a coupling enzyme for determining the enzymatic activity of various aminotransferases such as alanine aminotransferase (ALT) in UV spectrometry of the produced pyruvic acid, 2) as a coupling enzyme converting various substrates such as urea into pyruvic acid in UV spectrometry of the produced pyruvic acid, or 3) for eliminating endogenous pyruvic acid in a subject, etc. Particularly in the determination of aminotransferase activity using LDH as mentioned in 1) which is widely adopted as a clinical test, the recombinant cLDH-$B_4$ protein abundantly obtained by the present invention can be used. The determination of the enzymatic activity of transaminase using the recombinant cLDH-$B_4$ of the present invention can be carried out according to, for example, the method described in Japanese Patent Public Disclosure: No. 289/1996 cited above.

EXAMPLES

Example 1: Cloning of cDNA Encoding the Type B Subunit of Chicken LDH

The cDNA encoding the type B subunit of chicken LDH was cloned according to the procedure shown in FIG. 1.

1) Cloning of a partial fragment of cDNA encoding the type A subunit of chicken LDH PCR was performed on cDNA derived from liver of an adult female Leghorn (CLONTECH, QUICK-Clone™ cDNA) as a template using a sense primer corresponding to the amino acid sequence from the 98-position arginine to the 104-position serine and an antisense primer corresponding to the amino acid sequence from the 227-position lysine to the 233-position valine of the type A subunit (FIG. 2). The PCR reaction was run with 30 cycles of annealing at 55° C. for 0.5 minutes, polymerase reaction at 72° C. for 1.5 minutes and heat denaturation at 95° C. for 0.5 minutes.

The resulting PCR product was directly ligated to a vector by using PCR-Direct™ Cloning System (CLONTECH) to transform E. coli DH5α. The PCR product-ligated recombinant plasmid pDIRECT-cLDA was recovered from the transformants. As a result of DNA sequencing using pDIRECT-cLDA as a template, the ligated PCR product was found to be a partial fragment of the cDNA encoding the sequence of the 98th to 223rd amino acids of the type A subunit of chicken LDH.

2) Preparation of a cDNA probe

A cDNA fragment was excised by treating pDIRECT-cLDA with EcoRI/BamHI and then purified by using Glass-Max™ DNA Isolation Spin Cartridge System (GIBCO BRL). The purified cDNA fragment was labeled with $^{32}$P using BcaBest™ Labeling kit (TAKARA) to prepare a cDNA probe.

3) Screening of a cDNA library derived from chicken heart

The procedure was based on a manual of STRATAGENE.

(i) Plating cells (E. coli XL-1 Blue MRF') are infected with a cDNA library derived from chicken heart (made by STRATAGENE) to form plaques on a 150 mm plate.

(ii) Plaques are replicated from one plate onto two positively charged nylon membranes (Hybond-N+, made by Amersham) to prepare replica filters.

(iii) The replica filters are treated in the following order.
  a) Immersion in a solution of 1.5 M NaCl, 0.5 M NaOH for 7 minutes.
  b) Immersion in a solution of 1.5 M NaCl, 0.5 M Tris-HCl (pH 8.0) for 5 minutes twice.
  c) Immersion in a solution of 0.2 M Tris-HCl (pH 7.5), 2×SSC [20×SSC: 175.3 g/L NaCl, 88.2 g/L sodium citrate, pH 7.0] for 30 seconds.
  d) Dehydration with filter paper.
  e) UV irradiation for 5 minutes to immobilize DNA.

(iv) Thus treated replica filters are prehybridized at 42° C. for two hours in a prehybridization solution comprising 6×SSPE [20×SSPE: 175.3 g/L NaCl, 27.6 g/L $NaH_2PO_4.H_2O$, 7.4 g/L EDTA, pH 7.4], 5×Denhardt's solution [50×Denhardt's solution: 10 g/L Ficoll (Type 400; made by Pharmacia), 10 g/L polyvinyl pyrrolidone], 10 g/L bovine serum albumin (Fraction V; made by Sigma)], 10% dextran sulfate, 0.5% (w/v) SDS, 100 μg/ml denatured salmon sperm DNA fragments.

(v) The filters are hybridized at 42° C. overnight in the prehybridization solution containing a cDNA probe.

(vi) The filters are treated in the following order.
  a) Washing with 2×SSC solutions three times.
  b) Washing with a solution of 2×SSC, 0.1% SDS at 50° C. for 15 minutes twice.
  c) Dehydration with filter paper.

(vii) Autoradiography is run and the X-ray film is developed.

(viii) Signals on the X-ray film are compared with plaques to determine positive clones.

(ix) Plaques on the positive clones are cut out and vortexed in 1 ml of an SM solution [5.8 g/L NaCl, 2.0 g/L MgSO$_4$.7H$_2$O, 50 mM Tris-HCl (pH 7.5), 0.01% (w/v) gelatin] and 20 μl of chloroform to prepare a phage solution.

(x) Said phage solution is appropriately diluted to form plaques.

(xi) Then, the operations of (ii) to (viii) are repeated to purify the plaques.

Among about 10,000 plaques screened, six positive clones were obtained.

4) Recovery of recombinant plasmids from positive clones

The pBluescript SK(-) recombinant plasmids containing cDNA fragments were recovered from the six positive clones by automated excision operation.

(i) Plaques on the positive clones are cut out and vortexed in 500 μL of an SM solution and 20 μl of chloroform to prepare a phage solution.

(ii) Said phage solution is used for automated excision operation according to a manual of STRATAGENE.

(iii) The transformants of E. coli SOLR™ transformed with the pBluescript SK(-) recombinant plasmids containing cDNA fragments are obtained.

(iv) The recombinant plasmids are extracted from the transformants.

5) Determination of the nucleotide sequence of cDNA in the recombinant plasmids

The Sequences of cDNA in the six pBluescript SK(-) recombinant plasmids were determined from the both ends of each cDNA, respectively. The DNA sequence determination was performed with ABI373DNA Sequencer (made by Applied Biosystems). As a result, all the cDNAs in the six recombinant plasmids were presumed to be cDNA encoding the type B subunit of chicken LDH. Among them, the cDNA contained in the pBluescript SK(-)-cLDB8 was the longest and contained an initiation codon ATG.

6) Restriction mapping of cDNA

The pBluescript SK(-)-cLDB8 was digested with endonucleases PstI, XbaI, SacI, HincII and HindIII to prepare a restriction map of cDNA.

7) Subcloning of cDNA

The cDNA in the pBluescript SK(-)-cLDB8 was amplified using the primers shown in FIG. 4 and then ligated to pBluescript SK(-) to prepare a recombinant plasmid (pSK-cLDB8-E/B). Then, the cDNA fragment in pSK-cLDB8-E/B was divided into four fragments on the basis of the restriction map and each ligated to pBluescript SK(-).

8) Determination of the entire nucleotide sequence of cDNA

Figure 3:
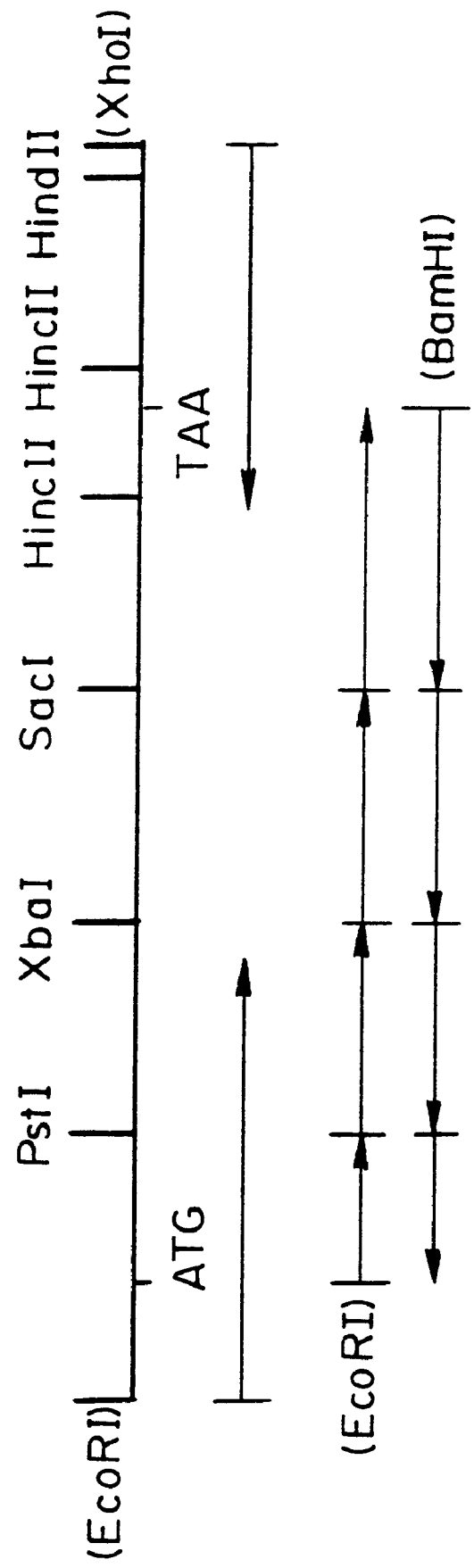
FIG. 3 shows a restriction map of the type B subunit of chicken LDH and a strategy for determining the entire nucleotide sequence.

The sequence of cDNA of a subclone was determined from both ends as shown in FIG. 3. As a result, the length of the cDNA was 1240 bp and encoded a sequence of 333 amino acids (FIG. 5). The amino acid sequence presumed from the nucleic acid sequence of cDNA (SEQ ID NO. 2) was identical with the amino acid sequence (SEQ ID NO. 3) directly sequenced from the chicken LDH-B$_4$ protein except for five amino acid residues numbered 10, 132, 207, 213 and 215 (FIG. 6). Therefore, it was concluded that the cloned cDNA is cDNA encoding the type B subunit of chicken LDH.

Example 2: Construction of an Expression Plasmid for the Type-B Subunit of Chicken LDH The cDNA in pSK-cLDB8-E/G was inserted into the Saccharomyces cerevisiae expression vector YRp1G (Japanese Patent Public Disclosure: No. 289267/1995 "Method for Enhancing Expression") to prepare an expression plasmid (YRp1G-cLD-B) (FIG. 7).

Example 3: Production of the Chicken LDH-B$_4$ Protein in a Synthetic Selection Medium and a Nutrient Medium In accordance with the method described in Japanese Patent Public Disclosure: No. 289267/1995 cited above, the cLDH-B$_4$ protein was produced. At first, Saccharomyces cerevisiae was transformed with the expression vector YRp1G-cLD-B prepared in Example 2. (The transformed yeast host cell was internationally deposited according to the Budapest Treaty under Accession No. FERM BP-5292.) Subsequently, the FERM BP-5292 cells were cultured in the synthetic selection medium and nutrient medium described in Japanese Patent Public Disclosure: No. 289267/1995 to produce the cLDH-B$_4$. The LD activity was evaluated by determining the variation in absorbance of cell extract at 340 nm according to the method described in Methods of enzymatic analysis, 3rd edn. vol. III pp. 118–126, which is incorporated herein as a reference. One unit (1U) of the enzyme is defined as the amount of the enzyme which causes a decrease of 1 μmol of NADH per one minute at 30° C.

Figure 8:
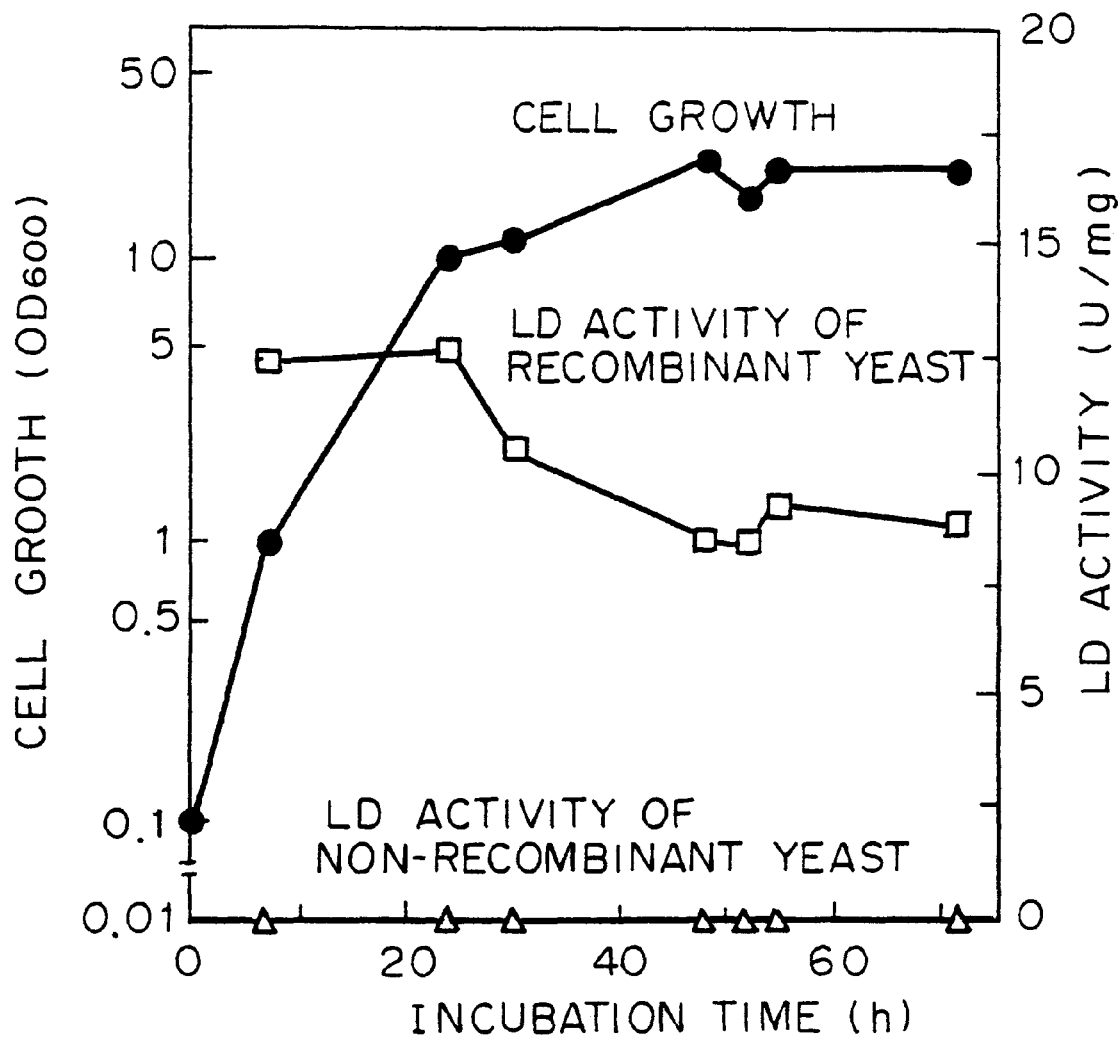
FIG. 8 shows the production of the recombinant chicken $LDH-B_4$ protein by *Saccharomyces cerevisiae*.

Example 4: Production of the Chicken LDH-B$_4$ Protein in a 16 L Fermentation Tank In accordance with the method described in Japanese Patent Public Disclosure: No. 289267/1995 cited above, the chicken LDH-B$_4$ was produced in a 16 L fermentation tank. As a result, 462 g of wet cells were obtained. The LD activity of an extract obtained by disrupting these cells was 8.9 U/mg (FIG. 8).

Example 5: Recombinant LDH-B$_4$ Protein

1) Preparation of a crude extract from the recombinant cells

The wet cells obtained in Example 4 were suspended in a 20 mM sodium phosphate buffer (pH 7.0) containing equal volumes of 5 mM β-mercaptoethanol and 1 mM EDTA and disrupted by a dinomill to prepare a crude extract.

2) Purification of the recombinant LDH-B$_4$ protein

Purification of the recombinant LDH-B$_4$ protein was carried out by modifying the method of Voorter et al. (Voorter, C. E. M. et al., (1993) Eur. J. Biochem. 211, 643–648). The crude extract was heat-treated at 60° C. for 20 minutes and the supernatant after centrifugation was fractionated with 35% ammonium sulfate at 4° C. overnight. The supernatant after centrifugation was fractionated with 70% ammonium sulfate at 4° C. for 3 hours to obtain a precipitate. The precipitate was suspended in a 20 mM sodium phosphate buffer (pH 7.0) containing a small amount of 1 mM EDTA so that it was dialyzed against said buffer. Then, affinity chromatography was run using a 5'-AMP Sepharose 4B column pre-equilibrated with a 20 mM sodium phosphate buffer (pH 7.0) containing 1 mM EDTA. Elution was done with the same buffer containing 0.25 mM NADH.

The following Table 1 shows the results of the purification of the recombinant chicken LDH-B$_4$ in each step.

TABLE 1

Purification of the recombinant chicken LD-B₄

| Step and fraction | Whole protein (mg) | Whole activity (kU) | Observed activity (%) | Specific activity (U/mg) | Purification degree (Fold) |
| --- | --- | --- | --- | --- | --- |
| Extraction: | | | | | |
| Crude extract (a) | 22,080 | 294 | (100) | 13.3 | (1.0) |
| Heat treatment (60° C., 20 min.): | | | | | |
| Supernatant 35% Ammonium sulfate fractionation: | 13,696 | 202 | 69 | 14.7 | 1.1 |
| Supernatant Dialysis after 70% ammonium sulfate fractionation: | 11,946 | 229 | 78 | 19.2 | 1.4 |
| Desalted sample 5'AMP Sepharose 4B: | 5,334 | 110 | 37 | 20.6 | 1.5 |
| Eluate (b) | 390 | 53 | 18 | 136 | 10 |

(a) Obtained from 455 g (wet weight) of the recombinant.
(b) Elution was done with a 20 mM sodium phosphate buffer (pH 7.0) containing 0.25 mM NADH and 1 mM EDTA.

As shown in Table 1, the affinity chromatography using a 5'-AMP Sepharose 4B column resulted in an approximately 10-fold purification of the recombinant LDH-B₄ protein with a yield of 18% and a specific activity of 136 U/mg. The purified LDH-B₄ protein showed essentially a single band at the position of a molecular size of about 38,000 by SDS-PAGE (FIG. 9).

Figure 9:
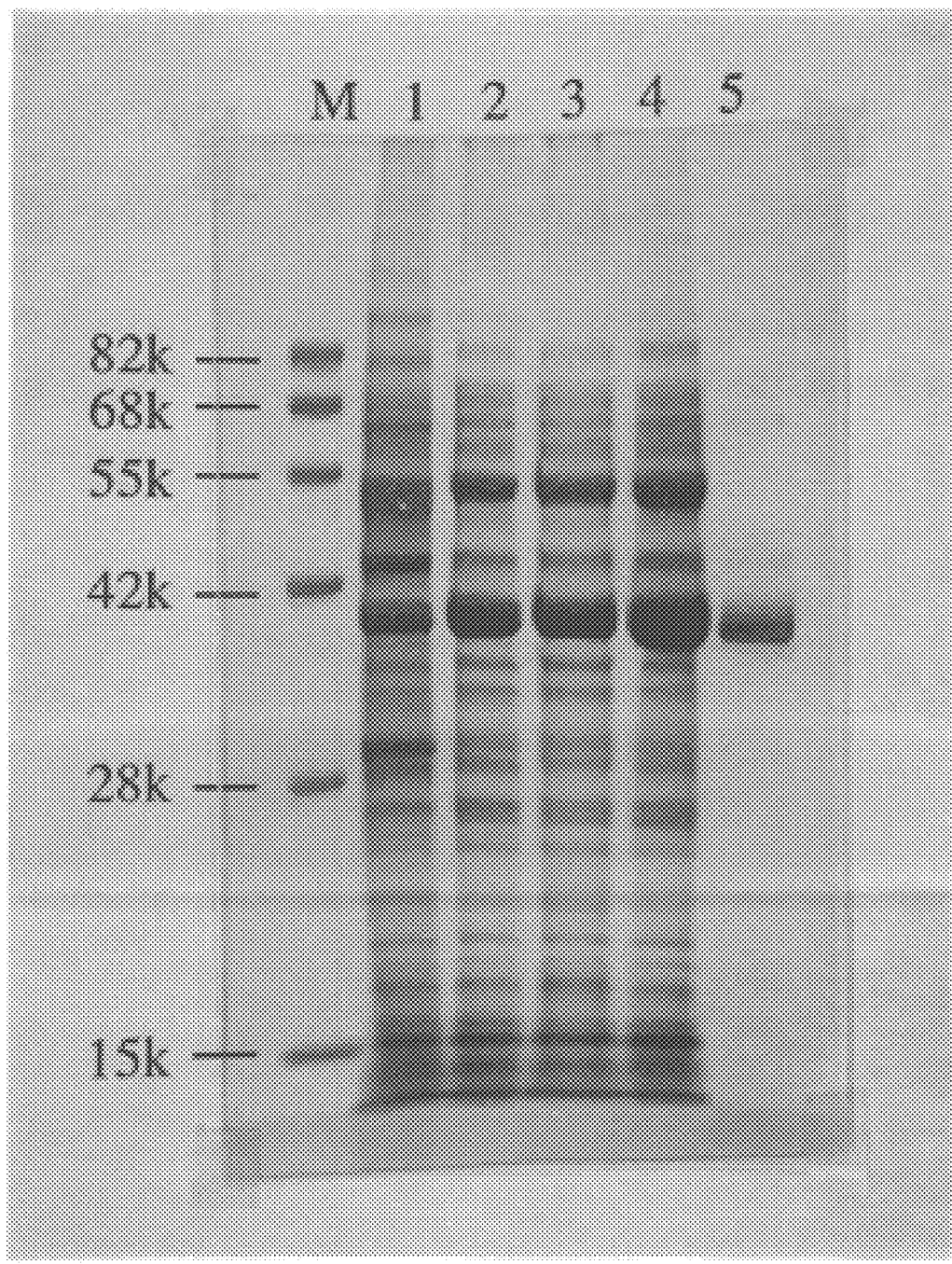
FIG. 9 shows the results of SDS-PAGE analysis of a purification step of the recombinant chicken $LDH-B_4$ protein.

FIG. 9 shows the results of SDS-PAGE analysis of the purification step of the recombinant chicken LDH-B₄ protein from the cell extract of the yeast *S. cerevisiae* (YRp1G-cLDB); lane 1, protein in the crude cell extract (20 μg); lane 2, protein in the supernatant after heat treatment (20 μg); lane 3, protein in the supernatant after 35% ammonium sulfate precipitation (20 μg); lane 4, protein in the dialysis sample after the 70% ammonium sulfate precipitate (20 μg); lane 5, protein in the eluate from the 5'-AMP Sepharose 4B column (2 μg). Lane M indicates an IgG-binding molecular weight marker.

Figure 10:
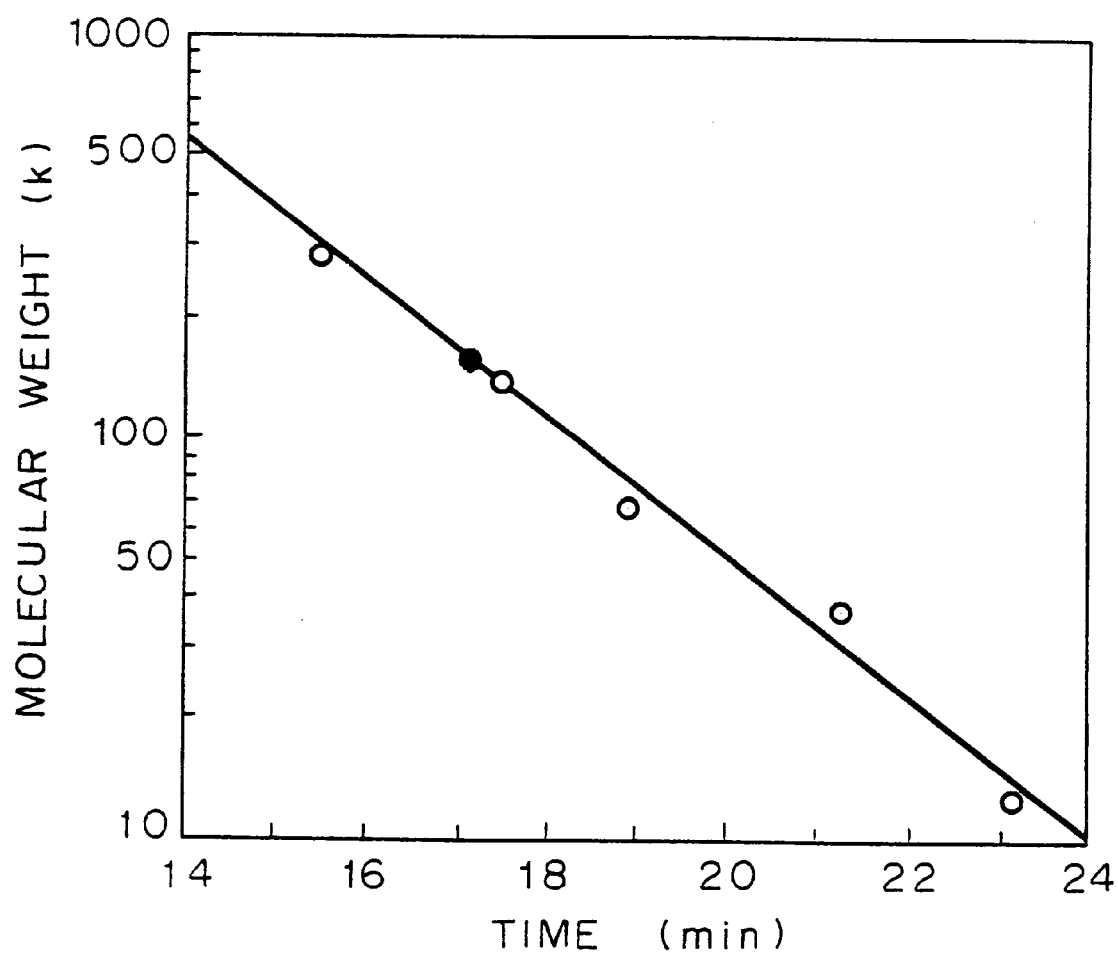
FIG. 10 shows the results of gel filtration column chromatography analysis of the molecular weight of the purified recombinant chicken $LDH-B_4$ protein.

3) Determination of the molecular weight of the recombinant chicken LDH-B₄ protein As a result of gel filtration column chromatography analysis of the purified sample by a SMART system (made by Pharmacia), the molecular weight of the purified recombinant chicken LDH-B₄ protein was about 147,000 (FIG. 10). It is presumed that the subunits B of chicken LDH are combined to form a tetramer (theoretical molecular weight of about 140,000) because the molecular weight of each subunit B of chicken LDH is calculated at about 36,000 from its amino acid sequence.

4) Amino acid sequence of the N-terminal of the recombinant chicken LDH-B₄ protein The amino acid sequence of the N-terminal of the recombinant chicken LDH-B₄ protein was analyzed. The sequence of 14 amino acids from the N-terminal was determined to be completely identical with the amino acid sequence presumed from the nucleotide sequence.

Example 6: Determination of Heat Stability of the Recombinant Chicken LDH-B₄

Figure 11:
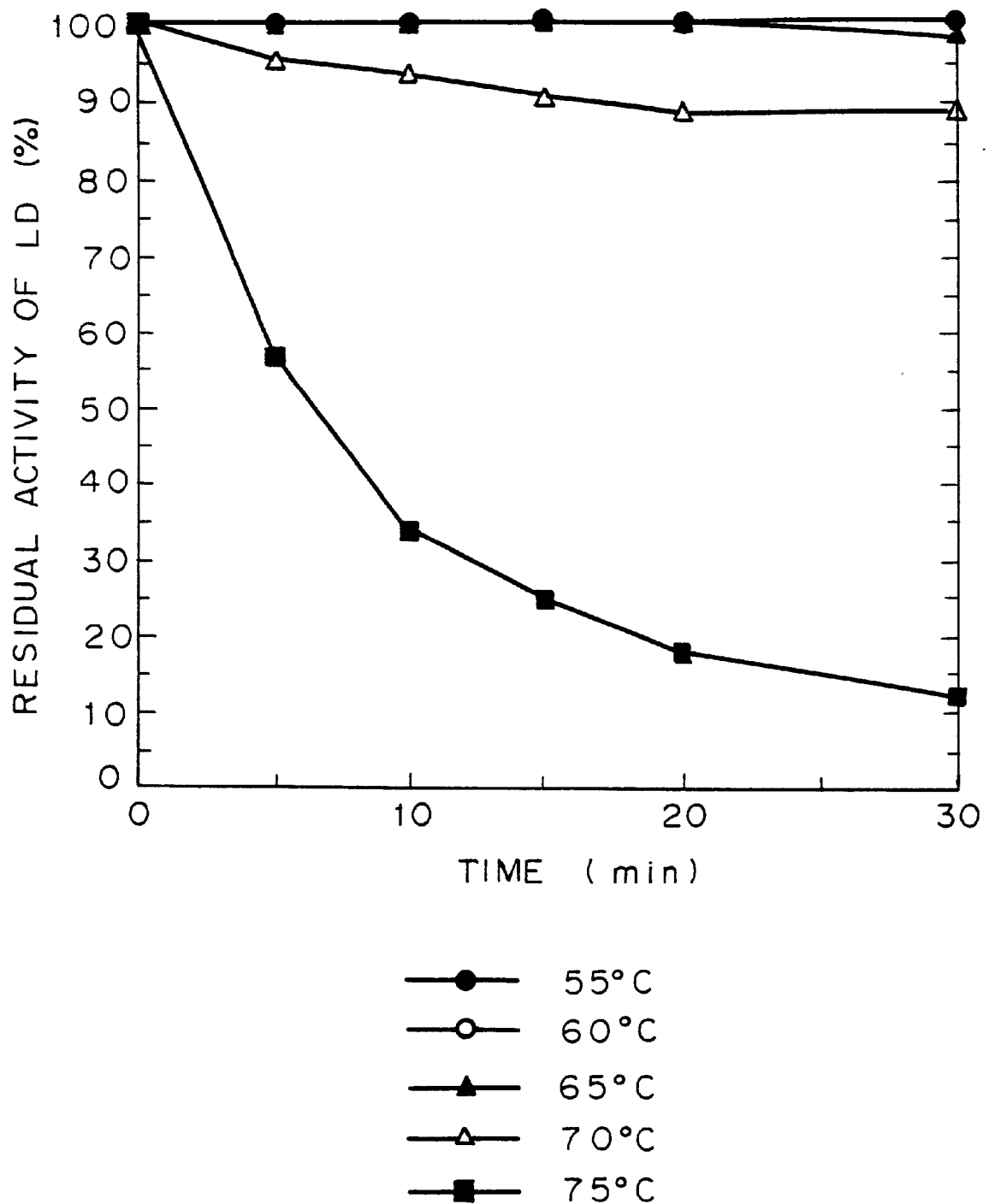
FIG. 11 shows the results of determination of the heat stability of the recombinant chicken $LDH-B_4$ protein.

The recombinant chicken LDH-B₄ was heat-treated at 55° C., 60° C., 65° C., 70° C. and 75° C. for 5, 10, 15, 20 and 30 minutes to determine the residual activity of LDH. As a result, the heat stability of the recombinant chicken LDH-B₄ showed the profile of FIG. 11, which was comparable to the heat stability of the natural chicken LDH-B₄.

As described above, an isolated gene encoding the type B subunit (cLDH-B) protein of chicken LDH has been provided according to the present invention. The cLDH-B protein can be provided in large amounts by transforming a host cell with said gene integrated in an expression vector so that said gene is expressed by said host cell. Said subunits form the tetrameric cLDH-B₄ isozyme, which can be used, for example, as a reagent for determining the activity of transaminase.

What is claimed is:

1. A pure recombinant avian lactate dehydrogenase protein having the amino acid sequence of SEQ ID NO: 2.

\* \* \* \* \*

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:

(A) LENGTH: 1240 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 55..1053

(xi) SEQUENCE DESCRIPTION: SEQ ID NO:1:

```
CCACGGTCAC GGTACTGCTC CCGGTTCTCC TTTCACCGCA CCGATCCGGA CGTT ATG        57
                                                            Met
                                                            1

GCG ACC CTG AAG GAG AAG CTG ATC GCC CCC GTG GCC GCG GGC AGC ACG       105
Ala Thr Leu Lys Glu Lys Leu Ile Ala Pro Val Ala Ala Gly Ser Thr
          5                  10                  15

GTT CCC AGC AAC AAG ATC ACC GTG GTG GGG GTC GGG CAG GTG GGG ATG       153
Val Pro Ser Asn Lys Ile Thr Val Val Gly Val Gly Gln Val Gly Met
             20                  25                  30

GCG TGT GCC ATC AGC ATC CTC GGC AAG GGT CTT TGT GAT GAG CTT GCT       201
Ala Cys Ala Ile Ser Ile Leu Gly Lys Gly Leu Cys Asp Glu Leu Ala
 35                  40                  45

CTG GTT GAT GTT TTG GAA GAC AAG CTA AAA GGA GAA ATG ATG GAT CTA       249
Leu Val Asp Val Leu Glu Asp Lys Leu Lys Gly Glu Met Met Asp Leu
 50                  55                  60                  65

CAG CAT GGC AGC TTG TTC CTT CAG ACT CAT AAG ATT GTG GCA GAC AAA       297
Gln His Gly Ser Leu Phe Leu Gln Thr His Lys Ile Val Ala Asp Lys
                 70                  75                  80

GAT TAT GCT GTC ACA GCC AAC TCC AAG ATT GTG GTA GTA ACT GCA GGT       345
Asp Tyr Ala Val Thr Ala Asn Ser Lys Ile Val Val Val Thr Ala Gly
             85                  90                  95

GTT CGT CAG CAA GAG GGG GAG AGT CGT CTC AAC CTG GTT CAG AGG AAT       393
Val Arg Gln Gln Glu Gly Glu Ser Arg Leu Asn Leu Val Gln Arg Asn
                100                 105                 110

GTG AAC GTC TTC AAA TTC ATC ATT CCT CAG ATT GTG AAA TAC AGC CCC       441
Val Asn Val Phe Lys Phe Ile Ile Pro Gln Ile Val Lys Tyr Ser Pro
            115                 120                 125

AAT TGC ACT ATC CTT GTG GTT TCC AAC CCA GTG GAT ATA TTA ACC TAT       489
Asn Cys Thr Ile Leu Val Val Ser Asn Pro Val Asp Ile Leu Thr Tyr
130                 135                 140                 145

GTC ACA TGG AAG CTG AGT GGC CTG CCA AAG CAC CGT GTG ATT GGA AGT       537
Val Thr Trp Lys Leu Ser Gly Leu Pro Lys His Arg Val Ile Gly Ser
                150                 155                 160

GGC TGC AAT CTA GAC ACA GCT AGA TTC CGC TAC CTG ATG GCT GAG AGA       585
Gly Cys Asn Leu Asp Thr Ala Arg Phe Arg Tyr Leu Met Ala Glu Arg
            165                 170                 175

CTT GGT ATC CAC CCA ACC AGC TGC CAT GGC TGG ATT TTA GGA GAA CAT       633
Leu Gly Ile His Pro Thr Ser Cys His Gly Trp Ile Leu Gly Glu His
        180                 185                 190

GGT GAT TCT AGT GTG GCT GTT TGG AGC GGA GTT AAT GTG GTA GGT GTT       681
Gly Asp Ser Ser Val Ala Val Trp Ser Gly Val Asn Val Val Gly Val
    195                 200                 205

TCT CTC CAG GAG CTG AAT CCT GCC ATG GGA ACT GAC AAA GAC AGC GAG       729
Ser Leu Gln Glu Leu Asn Pro Ala Met Gly Thr Asp Lys Asp Ser Glu
210                 215                 220                 225

AAC TGG AAG GAA GTC CAC AAG CAG GTT GTT GAA AGT GCC TAT GAG GTA       777
Asn Trp Lys Glu Val His Lys Gln Val Val Glu Ser Ala Tyr Glu Val
                230                 235                 240

ATC AGA CTC AAG GGG TAT ACG AAC TGG GCC ATT GGT CTT AGC GTT GCC       825
Ile Arg Leu Lys Gly Tyr Thr Asn Trp Ala Ile Gly Leu Ser Val Ala
```

-continued

```
                    245                     250                     255
GAG CTC TGT GAG ACA ATG CTG AAG AAC TTG TAC CGA GTT CAT TCT GTG           873
Glu Leu Cys Glu Thr Met Leu Lys Asn Leu Tyr Arg Val His Ser Val
            260                     265                     270

TCA ACA CTG GTA AAG GGC ACA TAT GGC ATT GAG AAC GAT GTC TTC CTG           921
Ser Thr Leu Val Lys Gly Thr Tyr Gly Ile Glu Asn Asp Val Phe Leu
        275                     280                     285

AGC CTG CCT TGT GTC CTG AGT GCC TCT GGA TTG ACA AGT GTC ATC AAC           969
Ser Leu Pro Cys Val Leu Ser Ala Ser Gly Leu Thr Ser Val Ile Asn
290                     295                     300                     305

CAA AAG CTG AAG GAT GAT GAA GTG GCT CAG CTG AAG AAG AGT GCA GAC          1017
Gln Lys Leu Lys Asp Asp Glu Val Ala Gln Leu Lys Lys Ser Ala Asp
                310                     315                     320

ACA TTG TGG AGC ATC CAG AAA GAT CTT AAA GAT CTG TAATTCAAAT               1063
Thr Leu Trp Ser Ile Gln Lys Asp Leu Lys Asp Leu
            325                     330

GTTAGATTGC AGCAATAGGA AAACAGCGTG TTGTGCACAA ATGTGGGCTC TCTACTCACT        1123

ATACATCTCT GTGGTTAACA TTTAATGCTC TTCCAGACTG AGCTTTTGTC CACGGTAGCT        1183

AAACATAAGC TTGCTGTAAC GCACAGACCT TATGAACAAA TAAAGCAACT TTCAGGC           1240
```

(2) INFORMATION FOR SEQ ID NO:2:

(i) SEQUENCE CHARACTERISTICS:
        (A) LENGTH: 333 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Thr Leu Lys Glu Lys Leu Ile Ala Pro Val Ala Ala Gly Ser
  1               5                  10                  15

Thr Val Pro Ser Asn Lys Ile Thr Val Val Gly Val Gly Gln Val Gly
                 20                  25                  30

Met Ala Cys Ala Ile Ser Ile Leu Gly Lys Gly Leu Cys Asp Glu Leu
             35                  40                  45

Ala Leu Val Asp Val Leu Glu Asp Lys Leu Lys Gly Glu Met Met Asp
         50                  55                  60

Leu Gln His Gly Ser Leu Phe Leu Gln Thr His Lys Ile Val Ala Asp
 65                  70                  75                  80

Lys Asp Tyr Ala Val Thr Ala Asn Ser Lys Ile Val Val Thr Ala
                     85                  90                  95

Gly Val Arg Gln Gln Glu Gly Glu Ser Arg Leu Asn Leu Val Gln Arg
                100                 105                 110

Asn Val Asn Val Phe Lys Phe Ile Ile Pro Gln Ile Val Lys Tyr Ser
            115                 120                 125

Pro Asn Cys Thr Ile Leu Val Val Ser Asn Pro Val Asp Ile Leu Thr
130                 135                 140

Tyr Val Thr Trp Lys Leu Ser Gly Leu Pro Lys His Arg Val Ile Gly
145                 150                 155                 160

Ser Gly Cys Asn Leu Asp Thr Ala Arg Phe Arg Tyr Leu Met Ala Glu
                165                 170                 175

Arg Leu Gly Ile His Pro Thr Ser Cys His Gly Trp Ile Leu Gly Glu
            180                 185                 190

His Gly Asp Ser Ser Val Ala Val Trp Ser Gly Val Asn Val Val Gly
        195                 200                 205
```

-continued

```
Val Ser Leu Gln Glu Leu Asn Pro Ala Met Gly Thr Asp Lys Asp Ser
    210                 215                 220

Glu Asn Trp Lys Glu Val His Lys Gln Val Val Glu Ser Ala Tyr Glu
225                 230                 235                 240

Val Ile Arg Leu Lys Gly Tyr Thr Asn Trp Ala Ile Gly Leu Ser Val
                245                 250                 255

Ala Glu Leu Cys Glu Thr Met Leu Lys Asn Leu Tyr Arg Val His Ser
            260                 265                 270

Val Ser Thr Leu Val Lys Gly Thr Tyr Gly Ile Glu Asn Asp Val Phe
        275                 280                 285

Leu Ser Leu Pro Cys Val Leu Ser Ala Ser Gly Leu Thr Ser Val Ile
    290                 295                 300

Asn Gln Lys Leu Lys Asp Asp Glu Val Ala Gln Leu Lys Lys Ser Ala
305                 310                 315                 320

Asp Thr Leu Trp Ser Ile Gln Lys Asp Leu Lys Asp Leu
                325                 330
```

(2) INFORMATION FOR SEQ ID NO:3:

(i) SEQUENCE CHARACTERISTICS:
        (A) LENGTH: 333 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

```
Met Ala Thr Leu Lys Glu Lys Leu Ile Thr Pro Val Ala Ala Gly Ser
1               5                   10                  15

Thr Val Pro Ser Asn Lys Ile Thr Val Val Gly Val Gly Gln Val Gly
                20                  25                  30

Met Ala Cys Ala Ile Ser Ile Leu Gly Lys Gly Leu Cys Asp Glu Leu
            35                  40                  45

Ala Leu Val Asp Val Leu Glu Asp Lys Leu Lys Gly Glu Met Met Asp
    50                  55                  60

Leu Gln His Gly Ser Leu Phe Leu Gln Thr His Lys Ile Val Ala Asp
65                  70                  75                  80

Lys Asp Tyr Ala Val Thr Ala Asn Ser Lys Ile Val Val Val Thr Ala
                85                  90                  95

Gly Val Arg Gln Gln Glu Gly Glu Ser Arg Leu Asn Leu Val Gln Arg
            100                 105                 110

Asn Val Asn Val Phe Lys Phe Ile Ile Pro Gln Ile Val Lys Tyr Ser
        115                 120                 125

Pro Asn Cys Val Ile Leu Val Val Ser Asn Pro Val Asp Ile Leu Thr
    130                 135                 140

Tyr Val Thr Trp Lys Leu Ser Gly Leu Pro Lys His Arg Val Ile Gly
145                 150                 155                 160

Ser Gly Cys Asn Leu Asp Thr Ala Arg Phe Arg Tyr Leu Met Ala Glu
                165                 170                 175

Arg Leu Gly Ile His Pro Thr Ser Cys His Gly Trp Ile Leu Gly Glu
            180                 185                 190

His Gly Asp Ser Ser Val Ala Val Trp Ser Gly Val Asn Val Ala Gly
        195                 200                 205

Val Ser Leu Gln Gln Leu Asp Pro Ala Met Gly Thr Asp Lys Asp Ser
    210                 215                 220
```

```
Glu Asn Trp Lys Glu Val His Lys Gln Val Val Glu Ser Ala Tyr Glu
225                 230                 235                 240

Val Ile Arg Leu Lys Gly Tyr Thr Asn Trp Ala Ile Gly Leu Ser Val
                245                 250                 255

Ala Glu Leu Cys Glu Thr Met Leu Lys Asn Leu Tyr Arg Val His Ser
                260                 265                 270

Val Ser Thr Leu Val Lys Gly Thr Tyr Gly Ile Glu Asn Asp Val Phe
            275                 280                 285

Leu Ser Leu Pro Cys Val Leu Ser Ala Ser Gly Leu Thr Ser Val Ile
            290                 295                 300

Asn Gln Lys Leu Lys Asp Asp Glu Val Ala Gln Leu Lys Lys Ser Ala
305                 310                 315                 320

Asp Thr Leu Trp Ser Ile Gln Lys Asp Leu Lys Asp Leu
                325                 330
```

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:4:

CCGGAATTCA TGGCGACCCT GAAGGAG                          27

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Met Ala Thr Leu Lys Glu
1               5
```

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:6:

CCCGGATCCC TATTACAGAT CTTTAAGATC                        30

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Leu Asp Lys Leu Asp
1               5

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:8:

CTGGTTCGGC CCACGTCAGC AAGAAGGAGA AAG                        33

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Arg Gln Gln Glu Gly Glu Ser
1               5

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

CTCGCTCGCC CAACCTGCTT GTGAACCTCC TT                          32

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Val Gln Lys His Val Glu Lys
1               5